(12) United States Patent
Lutz et al.

(10) Patent No.: US 10,509,001 B2
(45) Date of Patent: Dec. 17, 2019

(54) DEVICE FOR THE NMR ANALYSIS OF SUBSTANCES IN A SAMPLE, RESPIRATORY GAS ANALYSIS DEVICE, FUEL SENSOR AND METHOD

(71) Applicant: Robert Bosch GmbH, Stuttgart (DE)

(72) Inventors: Theresa Lutz, Ottobrunn (DE); Florian Einsele, Stuttgart (DE); Katrin Luckert, Leonberg (DE); Robert Roelver, Calw-Stammheim (DE)

(73) Assignee: Robert Bosch GmbH, Stuttgart (DE)

( * ) Notice: Subject to any disclaimer, the term of this patent is extended or adjusted under 35 U.S.C. 154(b) by 235 days.

(21) Appl. No.: 15/512,649

(22) PCT Filed: Aug. 20, 2015

(86) PCT No.: PCT/EP2015/069143
§ 371 (c)(1),
(2) Date: Mar. 20, 2017

(87) PCT Pub. No.: WO2016/045888
PCT Pub. Date: Mar. 31, 2016

(65) Prior Publication Data
US 2018/0202952 A1    Jul. 19, 2018

(30) Foreign Application Priority Data
Sep. 26, 2014  (DE) .................. 10 2014 219 561

(51) Int. Cl.
*G01N 24/08* (2006.01)
*G01R 33/32* (2006.01)
(Continued)

(52) U.S. Cl.
CPC ............. *G01N 24/08* (2013.01); *A61B 5/082* (2013.01); *A61B 5/097* (2013.01); *G01N 21/645* (2013.01);
(Continued)

(58) Field of Classification Search
CPC .... G01N 24/08; G01N 24/10; G01N 21/6486; G01N 21/645; G01N 33/497;
(Continued)

(56) References Cited

U.S. PATENT DOCUMENTS

| 3,693,071 A | 9/1972 | Dolbear |
| 2009/0275852 A1 | 11/2009 | Oki et al. |

(Continued)

FOREIGN PATENT DOCUMENTS

| CN | 102193074 A | 9/2011 |
| CN | 102575380 A | 7/2012 |

(Continued)

OTHER PUBLICATIONS

International Search Report corresponding to PCT Application No. PCT/EP2015/069143, dated Nov. 4, 2015 (German and English language document) (7 pages).

(Continued)

*Primary Examiner* — Susan S Lee
(74) *Attorney, Agent, or Firm* — Maginot, Moore & Beck LLP

(57) ABSTRACT

A device for analyzing substances in a sample on the basis of a measurement of nuclear magnetic resonances including a magnetic field device configured to generate a magnetic field. The device is configured such that, in order to detect magnetic resonances induced in the sample by the generation of the magnetic field, provision is made of at least one magnetic field sensor which comprises at least one sensitive component with diamond structures. The diamond structures have nitrogen vacancy centers.

15 Claims, 3 Drawing Sheets

(51) Int. Cl.
*G01N 33/22* (2006.01)
*A61B 5/08* (2006.01)
*A61B 5/097* (2006.01)
*G01N 21/64* (2006.01)
*G01N 33/497* (2006.01)
*G01R 33/26* (2006.01)
*G01R 33/31* (2006.01)

(52) U.S. Cl.
CPC ......... *G01N 21/6486* (2013.01); *G01N 33/22* (2013.01); *G01N 33/497* (2013.01); *G01R 33/26* (2013.01); *G01R 33/31* (2013.01); *G01R 33/323* (2013.01); *G01N 2021/6471* (2013.01)

(58) Field of Classification Search
CPC ............ G01N 33/22; G01N 2021/6471; A61B 5/097; A61B 5/082; G01R 33/302; G01R 33/24; G01R 33/31; G01R 33/26; G01R 33/323
See application file for complete search history.

(56) References Cited

U.S. PATENT DOCUMENTS

| | | | | |
|---|---|---|---|---|
| 2010/0308813 | A1* | 12/2010 | Lukin | G01R 33/032 324/244.1 |
| 2011/0062957 | A1 | 3/2011 | Fu et al. | |
| 2011/0120890 | A1 | 5/2011 | Macpherson et al. | |
| 2014/0077231 | A1 | 3/2014 | Twitchen et al. | |
| 2014/0340085 | A1* | 11/2014 | Cappellaro | G01R 33/1284 324/316 |
| 2015/0001422 | A1* | 1/2015 | Englund | G01N 21/6458 250/459.1 |
| 2015/0192532 | A1* | 7/2015 | Clevenson | G01N 24/006 324/304 |
| 2015/0374250 | A1* | 12/2015 | Hatano | A61B 5/04008 600/409 |
| 2015/0377865 | A1* | 12/2015 | Acosta | G01N 33/5091 435/7.1 |

FOREIGN PATENT DOCUMENTS

| | | |
|---|---|---|
| CN | 102906370 A | 1/2013 |
| CN | 103460068 A | 12/2013 |
| GB | 2483767 A | 3/2012 |
| WO | 2012/016977 A2 | 2/2012 |

OTHER PUBLICATIONS

Arai et al.; Fourier Magnetic Imaging with Nanoscale Resolution and Compressed Sensing Speed-up using Electronic Spins in Diamond; Jul. 3, 2015; 31 Pages; Massachusetts Institute of Technology, web.mit.edu/pcappell/www/pubs/Arai14x.pdf.

Laraoui et al.; High-resolution correlation spectroscopy of 13C spins near a nitrogen-vacancy centre in diamond; Nature Communications; Apr. 3, 2013; 7 Pages; Macmillan Publishers Limited.

Mamin et al.; Nanoscale Nuclear Magnetic Resonance with a Nitrogen-Vacancy Spin Sensor; Science Magazine; Feb. 1, 2013; pp. 557-560; vol. 339; www.sciencemag.org.

Acosta et al.; Broadband magnetometry by infrared-absorption detection of diamond NV centers and associated temperature dependence; Proc. of SPIE; Feb. 10, 2011; 9 Pages; vol. 7948.

Haw et al; Continuous Flow High Field Nuclear Magnetic Resonance Detector for Liquid Chromatographic Analysis of Fuel Samples; Analytical Chemistry; Dec. 1981; pp. 2327-2332; vol. 53, Issue No. 14; American Chemical Society.

Jelezko et al.; Single defect centres in diamond: A review; Physica Status Solidi (A) Applications and Materials; Oct. 11, 2006; pp. 3207-3225; vol. 203, Issue No. 13; Wiley InterScience, Weinheim, Germany.

Staudacher et al.; Nuclear Magnetic Resonance Spectroscopy on a (5-Nanometer)3 Sample Volume; Science Magazine; Feb. 1, 2013; pp. 561-563; vol. 339; www.sciencemag.org.

* cited by examiner

DEVICE FOR THE NMR ANALYSIS OF SUBSTANCES IN A SAMPLE, RESPIRATORY GAS ANALYSIS DEVICE, FUEL SENSOR AND METHOD

This application is a 35 U.S.C. § 371 National Stage Application of PCT/EP2015/069143, filed on Aug. 20, 2015, which claims the benefit of priority to Serial No. DE 10 2014 219 561.6, filed on Sep. 26, 2014 in Germany, the disclosures of which are incorporated herein by reference in their entirety.

The disclosure relates to a device for analysis of substances in a sample, wherein the analysis is based on a measurement of magnetic nuclear spin resonances, and to a respiratory gas analysis device, to a fuel sensor and to a method of analysis of substances in a sample.

BACKGROUND

Nuclear spin resonance spectroscopy (NMR spectroscopy, Nuclear Magnetic Resonance) is a frequently employed method of examining the electronic environment of individual atoms and the interactions of atoms with one another. This method is based on what is called magnetic nuclear spin resonance. This describes a resonant interaction between the magnetic moment of atomic nuclei present in a strong static magnetic field with a high-frequency magnetic alternating field. In this interaction, the atomic nuclei of a material sample absorb and emit electromagnetic alternating fields in a constant magnetic field. On the basis of characteristic frequency shifts in the spin precision caused by the magnetic moment of the nuclear spin, it is possible, for example, to conclude the binding state of particular isotopes in organic molecules. Nuclear spin resonance spectroscopy is capable in principle of detecting any organic compounds. However, the only isotopes amenable to spectroscopy are those which, in the ground state, have a non-zero nuclear spin and hence a magnetic moment. These include, for example, $^1H$ and $^{13}C$. On application of a static magnetic field, magnetic moments precess with a frequency which is characteristic of the particular atom and generally varies within a range between kHz and MHz. They thus emit a magnetic alternating field in the region of a few pT. Since the frequency of the alternating field, as well as the type of atom, is also dependent on the binding state of the atom, the binding states of the atom lead to frequency shifts in the region of a few Hz to 1000 Hz. Because of the limited sensitivity of magnetic field sensors, practical implementation is currently only possible with very large magnetic fields in order to polarize a sufficiently large number of spins that a sufficiently high measurement signal can be obtained with appropriate pulse excitation. The required magnetic fields, which have to reach up to 10 T, can be provided, for example, with superconducting magnets which are cooled with liquid nitrogen. For this reason, miniaturization of NMR instruments is generally impossible.

International patent application WO 2012/016977 A2 is concerned with a process for producing an optical element based on diamond. One possible application described for such an optical element is a magnetometer.

SUMMARY

The disclosure provides a device for analysis of substances in a sample based on a measurement of magnetic nuclear spin resonances, which is usable for a multitude of applications and in particular is also amenable to miniaturization. The device of the disclosure firstly has means of generating a reference magnetic field with which magnetic resonances are induced in the atoms of the substances in the sample. In addition, the device of the disclosure has at least one magnetic field sensor which is characterized in that it comprises at least one sensitive component with diamond structures, wherein the diamond structures have nitrogen vacancy centers (NV centers). The nitrogen vacancy centers in the diamond structure feature a readable electronic structure variable by the action of magnetic fields. These variations can be measured and constitute the basis for the analysis of the substances in the sample. The disclosure thus makes use of the properties of NV centers in diamond for measurement of nuclear spin resonances. Through the use of diamond structures with NV centers, it is possible to provide a very sensitive magnetic field sensor capable of measuring the magnetic alternating fields in the region of a few pT that can occur as nuclear spin resonances. It is already known from a scientific publication by Jelezko et al. (Phys. Stat. Sol. (a) 203, no. 13, 3207-3225 (2006)) that nitrogen vacancy centers (NV centers) in diamond have a characteristic electronic structure which can be excited by irradiation with microwaves and irradiation in the optical range and read again by detection of fluorescence emitted by the NV centers. The electronic structure depends on the lattice constant of the diamond crystal and also on magnetic field effects. The lattice constant is affected by temperature and by crystal stresses, and the crystal stresses can be altered, for example, by pressure effects. The inventors have been able to show that the electronic structure of the NV sites is very sensitive to external magnetic fields among other factors. More particularly, it is possible, given appropriate readout of the electronic structure, to measure magnetic fields with a sensitivity of up to 100 pT/√Hz. This very sensitive measurement principle is thus particularly suitable for the detection of nuclear spin resonances, it being possible to work with significantly weaker magnetic fields than customary to date.

Preferably, the magnetic field sensor of the device of the disclosure has at least one means of introducing electromagnetic excitation radiation in the optical range, especially within a wavelength range between about 530 nm and about 570 nm (green region of visible light), and at least one means of introducing electromagnetic radiation in the microwave range, especially within a frequency range between about 2000 MHz and about 4000 MHz. By excitation with electromagnetic radiation in the optical range and electromagnetic excitation in the microwave range, fluorescence emission is induced in the NV centers of the diamond structures, the spectrum of which is dependent on the active magnetic field, especially on the magnetic field strength. For detection of the fluorescence radiation emitted, the magnetic field sensor of the device of the disclosure also has at least one means of detection of the fluorescence radiation emitted. In order to facilitate the evaluation, at least one means of filtering electromagnetic radiation is additionally also provided, this preferably being an optical filter layer which is integrated into the magnetic field sensor and is intended for filtering of the excitation radiation out of the emitted fluorescence radiation.

Examples of means used for the introduction of electromagnetic radiation in the optical range may include an LED (light-emitting diode) and/or a VCSEL (vertical-cavity surface-emitting laser), i.e. a semiconductor laser as surface emitter. One example of a means that may be provided for introduction of electromagnetic radiation in the microwave range is a strip antenna. The strip antenna may be arranged, for example, directly on the sensitive component or in the immediate spatial proximity thereof. For the detection of the fluorescence radiation emitted, a photodiode is preferably provided, for example a p-n photodiode integratable into the sensor, which is particularly suitable for miniaturized applications.

The sensitive component is especially a diamond layer with NV centers or a correspondingly coated membrane. The NV centers of the diamond structures can be provided, for example, by NV doping of diamond.

In a particularly preferred configuration of the device of the disclosure, the magnetic field sensor comprises an arrangement of a plurality of sensitive components that are to be evaluated individually. The reason for this is that the detection volume in which a nuclear spin must be present around an NV center is very small, for example in the region of 25 $nm^3$. By virtue of the combination of several sensitive components that are to be evaluated individually, of several NV sensors as it were, it is therefore possible to improve the measurability. The size of the array can preferably be matched to the demands, especially to the required concentration sensitivity for a particular substance to be detected or for a particular molecular species.

In a preferred manner, the sensitive component, i.e. the diamond structures (diamond surfaces) of the sensitive component, may have structures for an increase in the surface area, for example needle-like or tube-like structures. In this way, it is possible to increase the detection volume per NV center, since structuring of the diamond surfaces provides structures which can be surrounded by the sample to be measured. Suitable surfaces may be provided, for example, by reactive ion etching, by means of which it is possible to produce the diamond tips, especially structured in the form of columns.

In a further preferred configuration of the device of the disclosure, the sensitive component has capillary structures. For a frequency resolution of a few Hz, a comparatively long measurement time is generally required. The provision of capillary structures achieves the effect that the sample to be measured resides for a sufficiently long period, for example in the period of a few seconds, in the detection volume of the NV center. Through structuring of capillaries or the like in the diamond surface, it is thus possible to retain the liquid sample in the region of the NV centers.

In a particularly appropriate configuration, the sensitive components may have at least one dedicated element for heating and/or cooling, for example a heatable Peltier element. By heating and especially by integrated heating, it is possible, for example, to remove, i.e. evaporate, the sample liquid from the sensitive component. If, for example, capillary structures are provided to retain the liquid sample, it is possible to evaporate the sample by heating the sensitive component after the measurement has ended. Integration of heating elements into the device of the disclosure can additionally be utilized for regeneration of the magnetic field sensor, for example by thermally destroying and removing adhering particles. In this way, it is possible to conduct a reset of the sensor.

Cooling of the sensitive component may be advantageous in order to provide a defined temperature again, especially after heating of the sensitive component, such that defined measurement conditions are established. Cooling of the sensitive component can especially also be advantageous for those applications in which condensation of gaseous samples is envisaged before the sample is analyzed in accordance with the disclosure. By means of cooling elements, it is possible to implement what is called a cold trap.

In a further preferred configuration of the device of the disclosure, the device comprises means of ionizing the sample. The reason for this is that the diamond surface, i.e. the surface of the sensitive component, generally has a negative surface charge. Through ionization of the sample, it is possible to promote surface adsorption at the charged diamond surface. The ionization of the sample can be achieved, for example, by strong electrostatic fields in the region of the sample inlet of the device. Ionization of the sample is advantageous especially in the case of gaseous samples.

In addition, it may advantageously be the case that the device comprises means of generating a positive potential in the sensitive component. For example, by application of a field plate on the reverse side of the diamond surface, it is possible to temporarily bring the sensitive component, i.e. the diamond layer, to a high positive potential, by means of which, on completion of measurement, it is possible to achieve the desorption of the substances from the sample and a sensor reset. In order to assure optical access through the sensitive component, this field plate may consist, for example, of transparent conductive oxide, for example of indium tin oxide or aluminum-doped zinc oxide.

The device of the disclosure is suitable for a multitude of applications because of its high measurement sensitivity and because of the range of substances to be detected, and also because of the robustness of the device owing to diamond, which is a very durable material per se. More particularly, the device of the disclosure can also be used under very difficult conditions, for example at high temperatures or in reactive media. The excitation of the sensitive component by electromagnetic radiation and the optical readout of the sensor additionally enables use in regions that are difficult to access, since no direct coupling to electronic elements is required by virtue of this manner of excitation and readout.

The device of the disclosure can be used, for example, for analysis of ingredients in food production and processing. With an analysis device of the disclosure, it is possible, for example, to detect and determine the alcohol content, the sugar content or the content of other substances.

Very particularly advantageously, the device of the disclosure can also be used for analysis of fuels and/or of lubricants and/or of hydraulic oils. In a preferred configuration of the analysis unit of the disclosure, the device is a fuel sensor, especially a fuel quality sensor.

The advancing developments in internal combustion engines and the associated ever more complex system components (for example injectors, exhaust gas aftertreatment systems, combustion chamber design and engine control systems) are resulting in a rising demand for fuel analysis systems which can detect, for example, constituents of biodiesel, water, sulfur, etc. in the fuel. Reliable information as to the nature and composition of the fuel is important for the adjustment of the engine control system, in order that the combustion process can be optimized. There is an increasing interest in modifying motor vehicles having internal combustion engines, for example, in such a way that they comply with the exhaust gas limits and standards stipulated in law irrespective of the fuel type and quality obtainable (called "flexible fuel" vehicles). For vehicles of this kind, in particular, on-board analysis of the fuel present in the tank is indispensable.

There are already various known fuel quality sensors that are based on concluding the composition of the particular fuel on the basis of absorption spectra measured. However, fuel quality sensors of this kind require technologically demanding and complex production of tunable optical filters and costly light sources that are needed for the spectroscopic resolution of the absorption characteristics. Moreover, it is difficult to detect any and all substances present in the fuel with a single sensor element, since not all substances affect the optical absorption in the fuel to an equal degree. Use of nuclear spin resonance spectroscopy for the analysis of fuel in a motor vehicle was not possible to date because of the high apparatus complexity and especially because of the high magnetic fields required. The fuel sensor of the disclosure, by contrast, provides a sensor based on the measurement of nuclear spin resonances which is usable in a motor vehicle. The fuel sensor of the disclosure, especially a fuel quality sensor which works with the device of the disclosure described, has the advantage that a single sensor device can be used to analyze the entire spectrum of possible fuel components. Moreover, a corresponding fuel quality sensor which works according to the disclosure is particularly suitable for miniaturization and is also very robust, such that it can be used advantageously in motor vehicles and even in combustion chambers.

The disclosure further encompasses a respiratory gas analysis device based on a measurement of magnetic nuclear spin resonances. The analysis device comprises a device according to the above description, wherein the device has means of generating a reference magnetic field and at least one magnetic field sensor based on the above-described measurement principle, which is intended for detection of magnetic resonances which are induced in the sample by the generation of the reference magnetic field. With regard to further features of the respiratory gas analysis device and especially the magnetic field sensor present therein, reference is made to the above description.

The analysis of the exhaled air (respiratory gas) is a non-invasive method within the scope of medical diagnosis. It is based on the fact that the lung imparts the metabolism between the blood circuit and respiratory air, and so constituents of the respiratory gas reflect biochemical processes in the body. For example, particular biomarkers which play a role within the context of early recognition or monitoring of the course and treatment of diseases are examined. Constituents of the respiratory gas are conventionally often analyzed by mass spectrometry methods, for which a high level of apparatus complexity is generally required. The analysis device of the disclosure, in terms of its use for a respiratory gas analysis device, by contrast, allows miniaturized analysis, which is ideally even portable. In this way, it is possible to achieve regular monitoring of the constituents of the respiratory gas that are relevant for the particular etiology for the patient.

In a preferred configuration of the respiratory gas analysis device, the device comprises means of condensing the exhaled respiratory air, especially a cold trap. With this measure, the respiratory gas is condensed, such that the downstream analysis can be based on the measurement of magnetic nuclear spin resonances in the liquid phase. Preferably, the cold trap may be in the region of the sensitive components of the magnetic field sensor. For example, a standard cooling element may be arranged beneath the sensitive component, such that the condensate is appropriately deposited directly on the diamond structures having the NV centers. The cooling element can be combined with a heating element. By means of a heating element, it is in turn possible to achieve removal of the adsorbed liquid after the measurement and a reset of the sensor. For this purpose, for example, a Peltier element with an integrated heater may be provided.

For example, such a respiratory gas analysis device can be utilized for the detection of hydrogen peroxide, which is considered to be an indicator of inflammation, in the respiratory gas. For example, significant increases in the hydrogen peroxide concentration were detected in the respiratory gas in patients having asthma bronchial or chronically obstructive lung disorders. There are already various known methods of detecting hydrogen peroxide in the respiratory gas, generally by undertaking condensation of the respiratory gas and subsequent liquid phase analysis. For example, amperometric measurements or optical methods are known. However, corresponding measurement apparatuses are designed for laboratory operation and cannot be operated by the patient him-/herself. Through the use of the analysis device of the disclosure in a respiratory gas analysis device, by contrast, a miniaturized form of such a device can be provided, which allows even the patient him-/herself to implement corresponding monitoring in daily life. Furthermore, the respiratory gas analysis device of the disclosure has the advantage that there is no need to keep a stock of reaction reagents or functionalized surfaces which would be spent after the reaction and would have to be replaced.

The respiratory gas analysis device of the disclosure is not restricted to a particular analyte. Instead, by adaptation of the evaluation, it is also possible to examine other analytes, for example hydrogen sulfide, which is considered to be an indicator of halitosis. In general, the respiratory gas analysis device can also be used for the analysis of other substances or molecules of diagnostic relevance. Suitable for this purpose are in principle, in particular, molecules containing hydrogen atoms (H) and/or carbon atoms (C), since $^1$H and $^{13}$C are isotopes having very good detectability with the magnetic nuclear spin resonance measurement used in accordance with the disclosure.

The disclosure further encompasses a method of analysis of substances in a sample based on a measurement of magnetic nuclear spin resonances. The method is characterized in that a magnetic field is generated, which generates magnetic resonances in the sample or in particular substances in the sample. Detection of the magnetic resonances generated is accomplished using diamond structures with nitrogen vacancy centers. Advantageously, on introduction of electromagnetic radiation in the optical range and on introduction of electromagnetic radiation in the microwave range, fluorescence radiation emitted by the diamond structures is evaluated as a measure of the magnetic resonances induced. Preferably, the electromagnetic radiation in the microwave range is introduced here with varying frequency. In the resulting fluorescence spectrum which is emitted by the NV centers of the diamond structures, the result is characteristic minima or drops in the fluorescence. These minima are evaluated in relation to the frequency of the microwave radiation. According to the active magnetic field, a particular shift in the fluorescence minima is induced. The position of the fluorescence minima within the fluorescence spectrum can thus be evaluated as a measure of the active magnetic field. With regard to further features of the method of the disclosure, reference is also made to the above description.

Further features and advantages of the disclosure will be apparent from the description of working examples which follows, in conjunction with the drawings. It is possible here for the individual features each to be implemented alone or in combination with one another.

DETAILED DESCRIPTION

The core of the disclosure is the exploitation of nitrogen vacancy centers in diamond for measurement of magnetic nuclear spin resonances, by means of which it is possible to provide very sensitive measurement devices which are especially also suitable for miniaturized applications.

Figure 1:
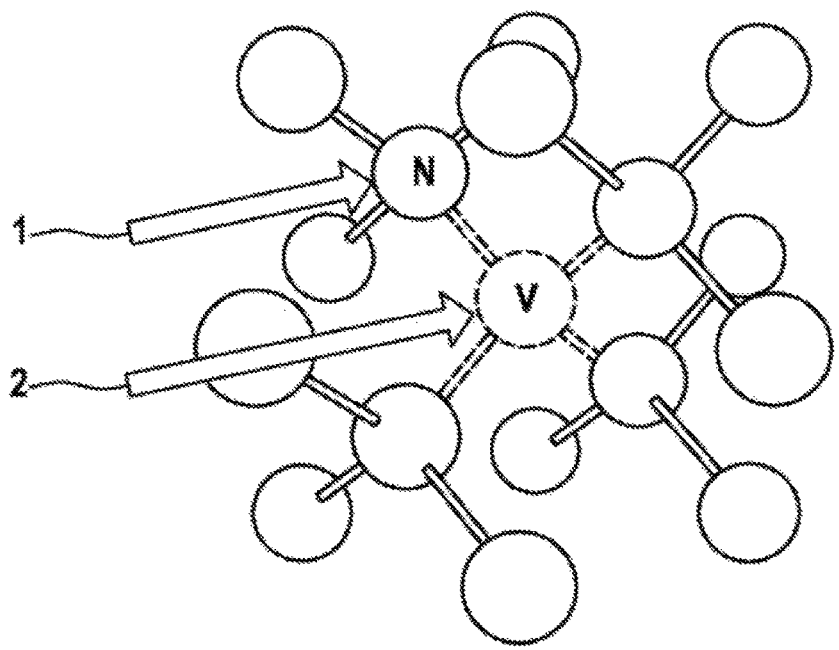
FIG. 1 a schematic diagram of a nitrogen vacancy center in diamond.

FIG. 1 illustrates the nitrogen vacancy center (NV center), which is known per se, in diamond. What is shown is the carbon atom lattice that forms the diamond structure. One of the carbon atoms is replaced by a nitrogen atom N (arrow 1). A directly adjacent carbon atom is missing in the diamond lattice. This is identified in this diagram by V (vacancy) (arrow 2). Such an NV center in diamond has a particular energy spectrum at room temperature. In the normal state, i.e. on excitation with light in the optical range and without further irradiation in the microwave range and without application of a magnetic field, the NV center on optical excitation shows fluorescence in the red wavelength range. If, as well as the optical excitation, microwave radiation is additionally also introduced, there is a measurable drop in the fluorescence, i.e. a fluorescence minimum, at a particular frequency, especially at 2.88 GHz. This phenomenon can be explained in that the electrons of the NV center in this case are raised from the level $m_s=\pm 1$ of the $^3A$ state to the level $m_s=\pm 1$ of the $^3E$ state and thence recombine in a non-radiative manner. On application of an external magnetic field, there is splitting of the level $m_s=\pm 1$ (Zeeman splitting), and, on application of the fluorescence across the frequency of the microwave excitation, two minima are observed in the fluorescence spectrum, the frequency separation of which is proportional to the magnetic field strength (Balasubramanian et al., Nature, vol. 455, page 648 (2008)). The magnetic field sensitivity is defined here by the minimum resolvable frequency shift and may reach up to 100 pT/√Hz. When the microwave frequency corresponds to the energy separation between the level $m_s=0$ and $m_s=\pm 1$, there is thus a drop in the fluorescence. In the case of an external magnetic field, there is a split in the level $m_s=\pm 1$, and two defined microwave frequencies at which the fluorescence decreases (minima) are observed. The frequency separation in the case of these defined microwave frequencies is proportional to the magnetic field, and so it is possible to infer the magnetic field strength by evaluation of the fluorescence minima.

Nuclear spin resonance spectroscopy, which is known per se, is based on the fact that many atoms or isotopes have a magnetic moment in their nuclear spin. These isotopes include the naturally occurring $^1H$ isotopes, for example in hydrogen peroxide ($H_2O_2$), and the $^{13}C$ isotope present in all organic compounds. These magnetic moments are aligned in a static manner without external excitation. Through application of an external magnetic field, these spins begin to precess and a magnetic alternating field with characteristic frequency occurs. The frequency can be assigned to the respective atomic species and the bonding state. The measurement principle underlying the disclosure detects the characteristic frequencies with the aid of a magnetic field sensor based on diamond structures with NV centers. The nuclear spin resonances are visible as noise in the fluorescence spectra of the NV centers. By specific pump-probe sequences, called "XY8N decoupling sequences", it is possible to filter the nuclear spin resonances out of the noise. The analysis of these noise spectra then allows, as in conventional nuclear spin resonance spectroscopy, a chemical analysis of the sample constituents. It has already been shown by Staudacher et al. (Science, vol. 339, pages 561-563 (2013)) that, for example, both distinction between $^{13}C$ and $^1H$ and distinction of various substances is possible by the measurement principle of the disclosure.

Figure 2:
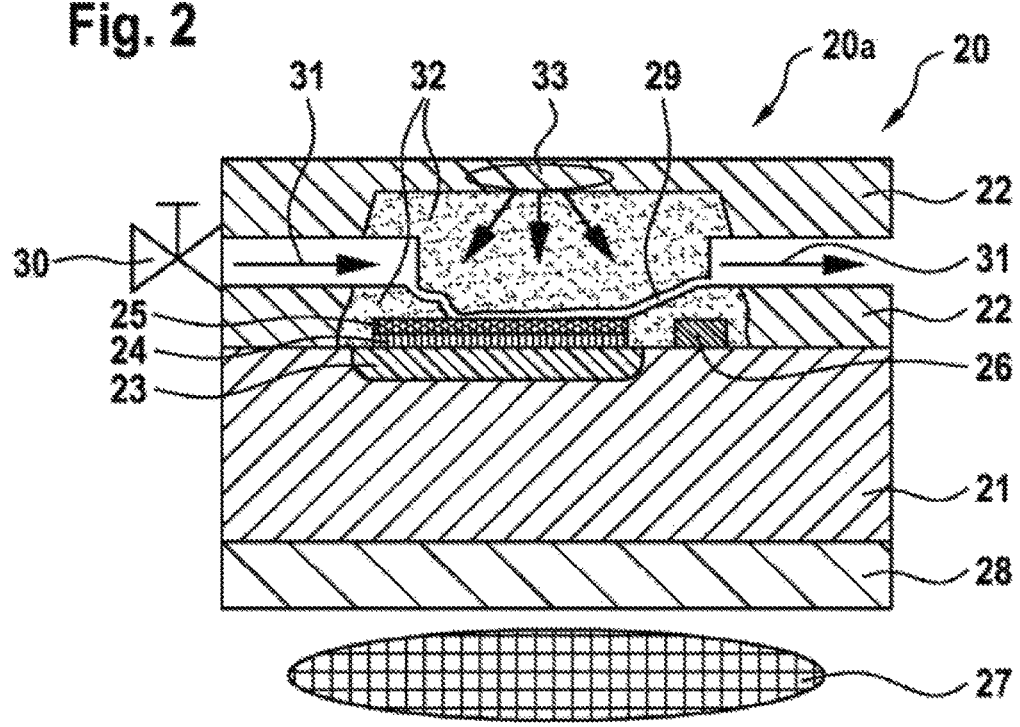
FIG. 2 a schematic section diagram of an embodiment of an analysis device of the disclosure as a monolithically integrated NMR sensor element for use as a fuel quality sensor.

FIG. 2 shows a possible embodiment of a monolithically integrated NMR sensor element of the disclosure as an analysis device 20 of the disclosure. Bonded to a carrier substrate 21, for example a silicon substrate, is an LED structure 22 with an integrated light source 33. Alternatively, rather than an LED structure, for example, a VCSEL laser chip may be provided. The light source 33 should preferably emit a wavelength in the green range of the visible light spectrum, especially in the wavelength range between about 530 nm and about 570 nm, since the photon absorption of the NV centers is at a maximum within this range. The carrier substrate 21 further comprises a photodiode 23, for example a p-n photodiode, or an arrangement of two or more photodiodes. Above the photodiode is an optical filter layer 24. Above the filter layer 24 is arranged a diamond layer 25 in admixture with NV centers as the sensitive component of the analysis device 20. In the spatial proximity of the diamond layer 25 is provided an RF antenna as means 26 of introducing the microwave radiation. In association with a voltage-controlled oscillator (VCO), the requisite electromagnetic excitation radiation in the microwave range can be introduced by the microwave antenna 26. The antenna 26 may, for example, be an RF strip antenna positioned at the edge of the photodiode array 23. In the case of simultaneous electromagnetic excitation radiation in the optical range by means of the light source 33, the characteristic nuclear spin resonances in the NV centers emit a characteristic fluorescence spectrum detectable via the photodiode 23. At the same time, the optical filter layer 24 filters the excitation light out of the fluorescence spectrum. The measurement signal which is then evaluated is the change in the fluorescence intensity on excitation with the pump-probe sequence (XY8N decoupling sequence).

Since the minimum resolvable frequency shift is connected to the lifetime of the excited spin states in the NV centers, it may be advantageous, for measurement of the nuclear spin resonances, to utilize the effect of coupling of NV electron spins to the N nuclear spin, and to transmit the frequency information to the N nuclear spin state with ml=1, which has a lifetime of days, whereas the lifetime of the excited spin states in the NV centers is in the region of milliseconds (Laraoui et al., Nature Comm., DOI: 10.1038/ ncomms2685). By means of this measure, it is possible in principle to resolve frequency shifts in the nuclear spin resonances to be measured of a few Hz.

The lower portion of the schematic section view shown shows a reference magnetic 27 which can provide, for example, a magnetic field with a strength of 100 mT. The reference magnet 27 is especially formed by a coil in the spatial proximity of the other components of the analysis device. By means of the magnet 27, the external magnetic field required for excitation of the characteristic spin precession is generated. Compared to standard NMR instruments, the reference magnet 27 can be much smaller, since, by contrast with conventional NMR, it is not necessary to synchronize a collective of identically directed nuclear spins in a relatively large sample volume; instead, individual nuclear spins in a small sample volume have to be read out.

Figure 5:
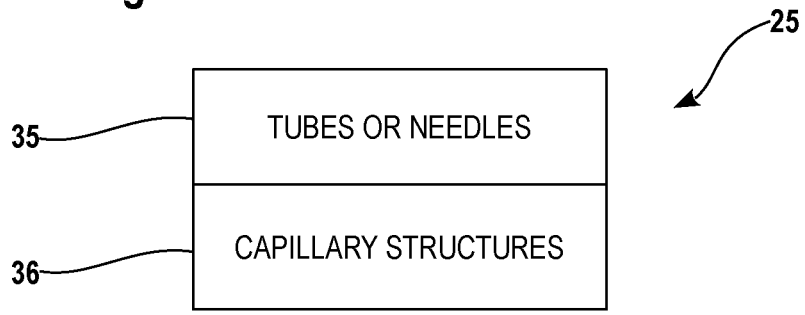
FIG. 5 a schematic diagram of an embodiment of the diamond layer of FIG. 2 schematically illustrating tubes or needles and a capillary structure.

Through structuring of the diamond layer 25, for example in the form of tubes or needles 35 (FIG. 5), it is possible to increase the surface area, by means of which the sensitivity can be increased. By means of capillary structures 36 (FIG. 5) in the diamond layer 25, the sample can be retained for a longer period of time, which allows the measurement time to be prolonged and hence the measurability to be improved.

The analysis device 20 further comprises an element 28 for heating and/or cooling. By heating the device on completion of measurement, it is possible, for example, to remove sample residues on the diamond layer 25. If the diamond layer 25 contains capillaries, for example, in order to retain a sample for longer, the sample liquid can be evaporated after the measurement by heating the device by means of the heating element 28. This can be utilized for regeneration of the sensor. Cooling by means of the element 28 can be used in order to re-establish defined measurement conditions after heating. In addition, cooling in the sense of a cold trap can be used in order to condense any gaseous sample.

Advantageously, a multitude of NV centers or NV sensors to be evaluated individually is present in the diamond layer 25. Correspondingly, the photodiode 23 can also be configured as an arrangement of two or more photodiodes. By means of this measure, the concentration sensitivity for a particular molecular species can be increased further.

The configuration of an analysis device 20 of the disclosure shown in FIG. 2 can especially be used as a fuel sensor 20a, for example as a fuel quality sensor. However, the analysis device of the disclosure is not restricted thereto. The liquid to be analyzed, i.e. the fuel, for example, is conducted over the diamond layer 25 through microfluidic channels 29. It may be preferable here that the liquid flow is interrupted during the measurement; this is achieved by switching an appropriate inlet valve 30. During the measurement, the inlet valve 30 is thus closed, in order to keep the liquid to be analyzed within the region of the sensitive component 25, i.e. of the diamond layer. After the measurement, the valve 30 is opened, such that the liquid to be analyzed in the channels 29 can be exchanged by virtue of a pressure differential between the inlet of the sensor in the region of the inlet valve 30 and between the opposite outlet, indicated here by an arrow 31. The material 32 which is permeated by the channels 29 is appropriately optically transparent, such that the optical excitation radiation from the light source 33 can reach the NV centers in the diamond layer 25 without significant losses.

Figure 3:
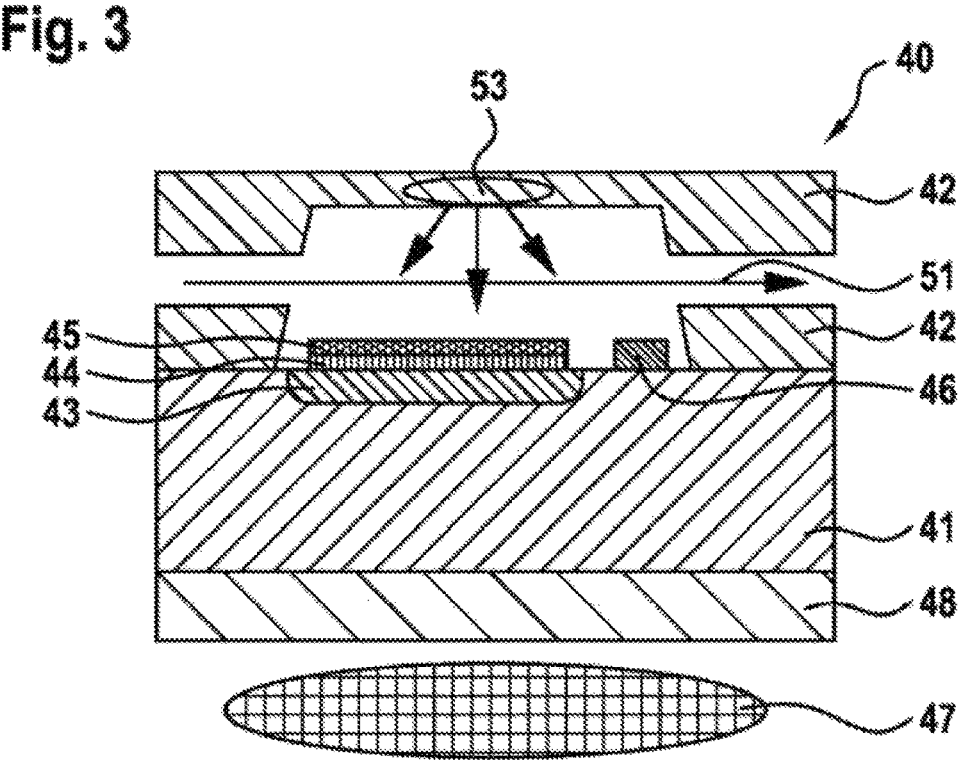
FIG. 3 a schematic section diagram of a further embodiment of an analysis device of the disclosure as a monolithically integrated NMR sensor element for use in an analysis device.

FIG. 3 illustrates a further example of an analysis device 40 of the disclosure, which can be integrated, for example, into a respiratory gas analysis device. In a comparable manner to the configuration illustrated in FIG. 2, the analysis device 40 comprises a carrier substrate 41 into which a photodiode array 43 is integrated. Above the region comprising the photodiode array 43 is an optical filter layer 44. Arranged atop the optical filter layer 44 is a diamond layer 45 with integrated NV centers (sensitive component). In the spatial proximity of the diamond layer 45 is a microwave antenna 46 for introduction of electromagnetic excitation radiation in the microwave range. Arranged atop the carrier substrate 41 is an LED structure 42 (or a VCSEL structure) with a light source 53 for emission of electromagnetic radiation in the optical range. The structure 42 is structured in such a way that the sample to be analyzed can flow through it, indicated here by the arrow 51. Beneath the carrier substrate 41 is an element 48 for cooling and heating of the analysis device 40. This may, for example, be a heatable Peltier element. In the spatial proximity of these structures is a magnet 47 intended to generate the reference magnetic field, in order to induce the spin precession and the magnetic resonances in the NV centers of the diamond layer 45. For the analysis device of the disclosure, for example, a magnetic field of B=100 mT is sufficient, since the measurement principle used in accordance with the disclosure via the NV centers in diamond is extremely sensitive. The overall dimensions of such a monolithically integratable NMR sensor structure may, for example, be about 5 cm×5 cm. Thus, the analysis device of the disclosure is very suitable for miniaturized applications. For example, such an analysis device may be incorporated into a handheld respiratory gas analysis device which can be used by a patient as required on an everyday basis.

Especially in the case of devices which are used for analysis of gaseous samples, for example respiratory gas, condensation of the gaseous sample is appropriately envisaged. In the case of the device 40, the element 48 can be used for this purpose to implement a cold trap. When the gaseous sample is conducted through the channels of the structure 42 (arrow 51), the carrier 41 is cooled together with the sensitive diamond layer 45 arranged thereon, such that the sample condenses directly on the diamond layer 45. The analysis can subsequently be effected in a liquid phase of the sample. On completion of measurement, particularly the region of the diamond layer 45 can be treated by means of the combined heating and cooling element 48, such that the condensate is removed again by evaporation, and the analysis device 40 can be prepared for a new measurement.

Figure 4:
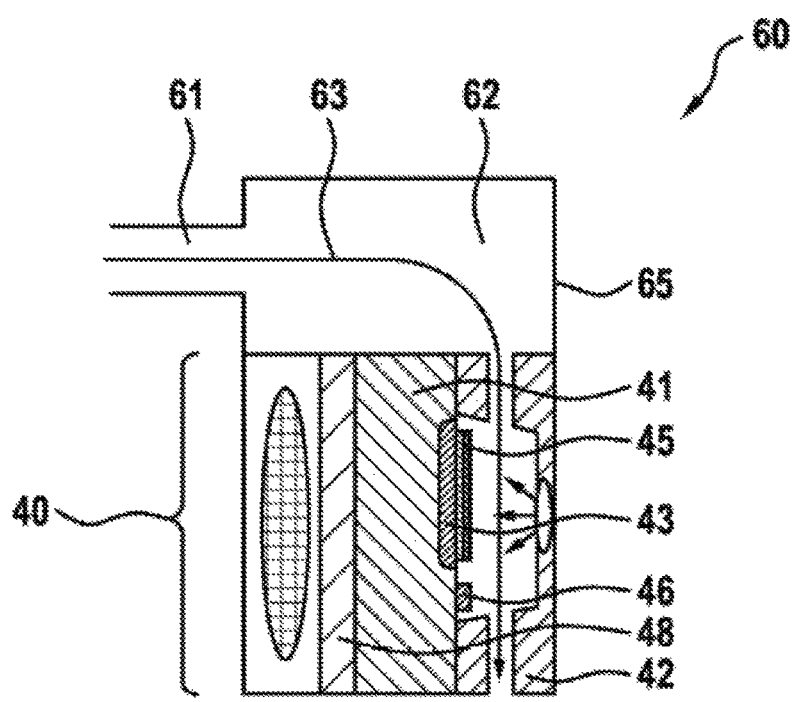
FIG. 4 a schematic diagram of a respiratory gas analysis device of the disclosure.

FIG. 4 illustrates the integration of the analysis device 40 from FIG. 3 into a respiratory gas analysis device 60. The respiratory gas analysis device has a mouthpiece 61 through which the exhaled respiratory air from a patient or from a user in general is blown into the device 60. For reasons of hygiene, the mouthpiece may be equipped with a microbial filter. The respiratory gas analysis device 60 further comprises an analysis chamber 62 which contains the analysis device 40 (measurement device) already elucidated with reference to FIG. 3. By means of corresponding conduction of an air flow 63 within the device via an air guide 65, the air arrives in the channel structures of the analysis device 40, such that the exhaled respiratory air (respiratory gas) is conducted across the diamond layer 45 of the analysis device 40. In this case, the combined heating and cooling element 48 provides a cold trap, such that the respiratory gas, when it arrives in the region of the diamond layer 45, condenses and can be analyzed in the liquid phase by the principle of the disclosure.

Figure 6:
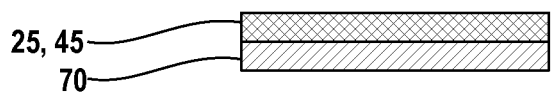
FIG. 6 a schematic diagram of a portion of another embodiment of an analysis device having a field plate.
Figure 7:
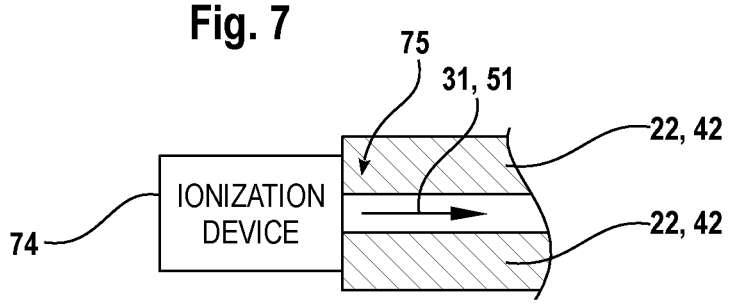
FIG. 7 a schematic diagram a portion of another embodiment of an analysis device having an ionization device.

In some embodiments the device comprises means of generating a positive potential in the sensitive component. For example, by application of a field plate 70 (FIG. 6) on the reverse side of the diamond surface 25, 45, it is possible to temporarily bring the sensitive component, i.e. the diamond layer 25, 45, to a high positive potential, by means of which, on completion of measurement, it is possible to achieve the desorption of the substances from the sample and a sensor reset. In order to assure optical access through the sensitive component, this field plate 70 may consist, for example, of transparent conductive oxide, for example of indium tin oxide or aluminum-doped zinc oxide.

In another configuration, the device comprises an ionization device 74 for ionizing the sample. The reason for this is that the diamond surface, i.e. the surface of the sensitive component, generally has a negative surface charge. Through ionization of the sample, it is possible to promote surface adsorption at the charged diamond surface. The ionization of the sample can be achieved, for example, by strong electrostatic fields in the region of the sample inlet 75 of the device. Ionization of the sample is advantageous especially in the case of gaseous samples.

The invention claimed is:

1. A device for analysis of substances in a sample based on a measurement of magnetic nuclear spin resonances, comprising:
   a magnetic field device configured to generate a magnetic field; and
   at least one magnetic field sensor configured to detect magnetic resonances induced in the sample by the magnetic field, the at least one magnetic field sensor including at least one sensitive component having diamond structures, the diamond structures including nitrogen vacancy centers,
   wherein the at least one sensitive component has needle structures or tube structures configured for surface enlargement.

2. A device for analysis of substances in a sample based on a measurement of magnetic nuclear spin resonances, comprising:
   a magnetic field device configured to generate a magnetic field; and
   at least one magnetic field sensor configured to detect magnetic resonances induced in the sample by the magnetic field, the at least one magnetic field sensor including at least one sensitive component having diamond structures, the diamond structures including nitrogen vacancy centers,
   wherein the at least one sensitive component has capillary structures.

3. A device for analysis of substances in a sample based on a measurement of magnetic nuclear spin resonances, comprising:
   a magnetic field device configured to generate a magnetic field; and
   at least one magnetic field sensor configured to detect magnetic resonances induced in the sample by the magnetic field, the at least one magnetic field sensor including at least one sensitive component having diamond structures, the diamond structures including nitrogen vacancy centers,
   wherein the at least one sensitive component has at least one Peltier element configured for heating and/or cooling.

4. The device as claimed in claim 3, wherein the at least one magnetic field sensor further includes at least one first electromagnetic device configured to introduce electromagnetic excitation radiation in an optical range, at least one second electromagnetic device configured to introduce electromagnetic radiation in a microwave range, and at least one detection device configured to detect emitted fluorescence radiation.

5. The device as claimed in claim 4, wherein:
   the electromagnetic excitation radiation in the optical range has a wavelength range of 530 nm to 570 nm, and
   the electromagnetic radiation in the microwave range has a frequency range of 2000 MHz to 4000 MHz.

6. The device as claimed in claim 3, wherein:
   the at least one sensitive component is included in a plurality of sensitive components,
   the at least one magnetic field sensor further includes an arrangement of the plurality of sensitive components, and
   each sensitive component of the plurality of sensitive components is configured for individual evaluation.

7. A device for analysis of substances in a sample based on a measurement of magnetic nuclear spin resonances, comprising:
   a magnetic field device configured to generate a magnetic field; and
   at least one magnetic field sensor configured to detect magnetic resonances induced in the sample by the magnetic field, the at least one magnetic field sensor including at least one sensitive component having diamond structures, the diamond structures including nitrogen vacancy centers; and
   an ionization device configured to ionize substances in the sample.

8. A device for analysis of substances in a sample based on a measurement of magnetic nuclear spin resonances, comprising:
   a magnetic field device configured to generate a magnetic field; and
   at least one magnetic field sensor configured to detect magnetic resonances induced in the sample by the magnetic field, the at least one magnetic field sensor including at least one sensitive component having diamond structures, the diamond structures including nitrogen vacancy centers; and
   a generating device configured to generate a positive potential in the at least one sensitive component.

9. A respiratory gas analysis device, comprising:
   a mouthpiece configured to receive exhaled respiratory air;
   an air guide; and
   an NMR device fluidly connected to the mouthpiece via the air guide and configured to analyze substances in a sample based on a measurement of magnetic nuclear spin resonances, the NMR device including (i) a magnetic field device configured to generate a magnetic field, and (ii) at least one magnetic field sensor configured to detect magnetic resonances induced in the sample by the magnetic field, the at least one magnetic field sensor including at least one sensitive component having diamond structures, the diamond structures including nitrogen vacancy centers.

10. The respiratory gas analysis device as claimed in claim 9, wherein the at least one magnetic field sensor further includes:
    at least one first electromagnetic device configured to introduce electromagnetic excitation radiation in an optical wavelength range of 530 nm to 570 nm;
    at least one second electromagnetic device configured to introduce electromagnetic radiation in a microwave frequency range of 2000 MHz to 4000 MHz; and at least one detection device configured to detect emitted fluorescence radiation.

11. A respiratory gas analysis device, comprising:
an NMR device configured to analyze substances in a sample based on a measurement of magnetic nuclear spin resonances, the NMR device including (i) a magnetic field device configured to generate a magnetic field, and (ii) at least one magnetic field sensor configured to detect magnetic resonances induced in the sample by the magnetic field, the at least one magnetic field sensor including at least one sensitive component having diamond structures, the diamond structures including nitrogen vacancy centers; and
a condensing device configured to condense exhaled respiratory air and to cool the sensitive component.

12. The respiratory gas analysis device as claimed in claim 11, wherein the condensing device is a cold trap.

13. A respiratory gas analysis device, comprising:
an NMR device configured to analyze substances in a sample based on a measurement of magnetic nuclear spin resonances, the NMR device including (i) a magnetic field device configured to generate a magnetic field, and (ii) at least one magnetic field sensor configured to detect magnetic resonances induced in the sample by the magnetic field, the at least one magnetic field sensor including at least one sensitive component having diamond structures, the diamond structures including nitrogen vacancy centers,
wherein the respiratory gas analysis device is configured to measure hydrogen peroxide and/or hydrogen sulfide.

14. A device for analysis of substances in a sample based on a measurement of magnetic nuclear spin resonances, comprising:
a magnetic field device configured to generate a magnetic field; and
at least one magnetic field sensor configured to detect magnetic resonances induced in the sample by the magnetic field, the at least one magnetic field sensor including at least one sensitive component having diamond structures, the diamond structures including nitrogen vacancy centers,
wherein the device is a fuel sensor.

15. A device for analysis of substances in a sample based on a measurement of magnetic nuclear spin resonances, comprising:
a magnetic field device configured to generate a magnetic field; and
at least one magnetic field sensor configured to detect magnetic resonances induced in the sample by the magnetic field, the at least one magnetic field sensor including at least one sensitive component having diamond structures, the diamond structures including nitrogen vacancy centers, wherein:
the at least one magnetic field sensor further includes at least one first electromagnetic device configured to introduce electromagnetic excitation radiation in an optical range, at least one second electromagnetic device configured to introduce electromagnetic radiation in a microwave range, and at least one detection device configured to detect emitted fluorescence radiation,
the at least one magnetic field sensor further includes at least one filtering device configured to filter electromagnetic radiation, and
the at least one filtering device includes at least one optical filter layer configured to filter the excitation radiation out of the emitted fluorescence radiation.

* * * * *